United States Patent [19]
Murphy et al.

[11] Patent Number: 5,998,634
[45] Date of Patent: Dec. 7, 1999

[54] ONE-STEP SYNTHESIS OF VITAMIN-C (L-ASCORBIC ACID)

[75] Inventors: Andrew P. Murphy, Littleton; Lisa Renee Henthorne, Evergreen, both of Colo.

[73] Assignee: The United States of America as represented by the Secretary of the Interior, Washington, D.C.

[21] Appl. No.: 09/270,194

[22] Filed: Mar. 15, 1999

[51] Int. Cl.⁶ .................................................. C07D 307/62
[52] U.S. Cl. ............................................................. 549/315
[58] Field of Search ............................................ 549/315

[56] References Cited

U.S. PATENT DOCUMENTS

| | | | |
|---|---|---|---|
| 4,491,668 | 1/1985 | Ikawa et al. | 549/315 |
| 5,391,770 | 2/1995 | Le Fur et al. | 549/315 |
| 5,744,618 | 4/1998 | Fechtel et al. | 549/315 |

*Primary Examiner*—Amelia Owens
*Attorney, Agent, or Firm*—E. Philip Koltos

[57] ABSTRACT

A method is provided for producing L-ascorbic acid (Vitamin-C) in a single process step. Starting material, particularly a mixture of compounds from the group consisting of glucose, sorbitol, sorbose, and 2-keto-L-gulonic acid, is catalytically oxidized in aqueous solution by hypochlorous acid. L-ascorbic acid then can be separated from the aqueous solution, and the unconverted reactants recycled for greater conversion. The reaction occurs in the aqueous state at ambient temperature near a pH of 5.5 when an optimum amount of hydrous cobalt-oxide is present in the solution.

12 Claims, No Drawings

ONE-STEP SYNTHESIS OF VITAMIN-C (L-ASCORBIC ACID)

FIELD OF THE INVENTION

The present invention relates to the field of synthesizing ascorbic acid from glucose, sorbitol, sorbose, and 2-keto-gulonic acid. More specifically, the invention relates to producing L-ascorbic acid (vitamin-C) from D-glucose in a single process step involving oxidation with hypochlorous acid in the presence of hydrous cobalt oxide catalyst.

BACKGROUND OF THE INVENTION

Manufacturing of L-ascorbic acid (Vitamin-C) is currently based on the synthesis developed by Reichstein and patented in 1936 (U.S. Pat. No. 2,056,126). Over the years, advances in science and technology have led to numerous technical modifications which have improved the efficiency in the production of Vitamin-C and have been incorporated into the Reichstein-Grussner synthesis which is the predominant method used in industry today. The Reichstein-Grussner synthesis involves five distinct steps: catalytic hydrogenation, bacterial fermentation, acid promoted reaction with acetone, catalytic oxidation, and acid hydrolysis (see Kirk-Othmer "Encyclopedia of Chemical Technology", 4th ed., John Wiley & Sons, New York, 1992). The steps of the aforementioned process are such that the synthesis requires the addition of various chemicals (including strong acids and bases), multiple stages of by-product separation, the treatment and disposal of environmentally toxic wastes, and extensive process control mechanisms. Accordingly, the synthesis is very costly. Thus, various attempts have been made to devise a new, more economical and efficient way to manufacture Vitamin-C.

To date, the prior art has concentrated on reducing the cost of synthesizing L-ascorbic acid by increasing the efficiency of, and reducing the cost of, a particular step in the Reichstein-Grussner synthesis. U.S. Pat. No. 2,190,377 to Dalmer et al. discloses a catalytic reaction for converting L-sorbose into 2-keto-L-gulonic acid ("L-KGA"). This method entails reacting an alkaline solution of sorbose with gaseous oxygen in the presence of platinum or palladium metal. This approach condenses two of the five steps of the Reichstein-Grussner synthesis into one step, but still leaves an intricate, multi-step process for vitamin-C synthesis.

U.S. Pat. No. 2,165,151 to Pasternack et al. discloses a method of oxidizing L-KGA to L-ascorbic acid without the use of strong acids or bases as is traditionally used in the last step of the Reichstein-Grussner synthesis. The method involves introducing fine metal filings, including cobalt, into an aqueous solution of KGA. The solution is then heated and agitated to reach fifty percent conversion to vitamin-C.

The foregoing and other alterations to the currently used Reichstein-Grussner synthesis have failed to eliminate aforementioned drawbacks of vitamin-C synthesis in a cost-effective manner so as to be commercially viable.

It is, therefore, an object of the invention to provide a single-step synthesis of L-ascorbic acid from D-glucose such that vitamin-C may be produced in a cost-effective manner.

SUMMARY OF THE INVENTION

Before describing the invention, it is of interest to note by way of further background that U.S. Pat. No. 5,244,581 to Murphy (one of the co-inventors here) teaches the use of hypochlorous acid to oxidize aqueous formaldehyde, found in waste water, in the presence of a cobalt oxide catalyst. The oxidation of formaldehyde was found to proceed at a rapid rate using this system in a slightly acidic solution at room temperature. However, the hydrous cobalt oxide-hypochlorous acid system does not result in any substantial oxidation of other organic compounds. As a result, it was considered that such a system would have potential as a selective oxidant of an $\alpha$-hydroxy acid group to an $\alpha$-keto acid group in large organic molecules. An example of this reaction was found to occur in the synthesis of sorbose from sorbitol, a single step in the production of vitamin-C.

As will be further described in the description of the preferred embodiments hereinbelow, according to one aspect of the invention, hypochlorous acid in the presence of hydrous cobalt oxide catalyst has been found to convert sorbitol to sorbose. It has also been discovered that this catalytic reagent further oxidizes sorbose to 2-keto-gulonic acid ("KGA"), and then further to ascorbic acid. Additionally, the hydrous cobalt oxide-hypochlorous acid system has been found to oxidize glucose to sorbitol. These discoveries are the basis of the present invention and are used to reduce the synthesis of vitamin-C from D-glucose to a single reaction step comprising reacting aqueous D-glucose with hypochlorous acid in the presence of hydrous cobalt oxide. The reaction has been found to proceed near ambient temperatures at about a pH between 4 and 6.5.

More generally, in accordance with the present invention, a process is provided for producing ascorbic acid from a compound selected from the group consisting of glucose, sorbitol, sorbose, and 2-keto-gulonic acid, the process comprising: oxidizing the compound with an effective amount of hypochlorous acid in the presence of a catalyst to produce ascorbic acid.

Preferably, the hypochlorous acid is present in a stoichiometric amount, and more preferably, the hypochlorous acid and the compound are present in a molar ratio between about 1:1 and about 3:1, and most preferably, the hypochlorous acid and the compound are present in a molar ratio of about 1:1. However, in general, the amount of acid can be greater or less depending on the results produced. More specifically, if too much acid is used, the acid will dissolve the hydrous cobalt catalyst, and this is undesirable. On the other hand, if too little acid is used, the yield may be low and this is also undesirable.

The catalyst is preferably an oxide of cobalt.

Advantageously, the oxidation occurs at a temperature in the range from about 1° C. to 99° C.

Further, the oxidation preferably occurs in an aqueous phase. As stated above, the aqueous phase is maintained at about a pH between 4 and 6.5, and most preferably, the aqueous phase is maintained at a pH of about 5.5.

Other features and advantages of the invention will be set forth in, or apparent from, the detailed description of the preferred embodiments of the invention which is found herein below.

DESCRIPTION OF THE PREFERRED EMBODIMENTS

The invention uses a hydrous oxide of cobalt as a catalyst to increase the rate of oxidation of glucose, sorbitol, sorbose, and KGA to ascorbic acid. The cobalt commonly employed in the practice of the invention can be from any 2+ or 3+ salt of cobalt, or even finely ground cobalt metal. The cobalt is then converted to a hydrous oxide of cobalt, in the form of a precipitate, by the addition of the sodium salt of hypochlorous acid, NaOCl, or by addition of aqueous hypochlorous acid. Aqueous mixtures of the compounds glucose, sorbitol, sorbose, and KGA can then be added to this hydrous cobalt oxide-hypochlorous acid catalytic system and agitated, resulting in significant oxidation of the organic compounds to ascorbic acid or other co-products. The pH of the system is maintained at about between 4 and 6.5, preferably at about 5.5, by the continuous addition of hypochlorous acid. Another desirable aspect of the oxidation is that it acheives a satisfactory conversion at room temperature, but the oxidation temperature can range anywhere from about 1° C. to about 99° C. The produced ascorbic acid can then be separated from the product solution, and the co-products can be recycled for further cobalt oxide-hypochlorous acid oxidation to produce more ascorbic acid. Additionally, the precipitate form of the hydrous cobalt oxide catalyst allows it to be easily separated from the products such that it can be used repeatedly. The following examples are intended to demonstrate the aspects and certain advantages of the invention in practice, but in no way limit the scope of the invention. All of the data presented in the examples were obtained at ambient temperatures (approximately 25° C.).

EXAMPLE I

Approximately 2.5 mL of 10% $COCl_2*6H_2O$, corresponding to about 1.04 mmole of Co, was added to 100 mL of deionized water in a beaker. Then, 5 g of sorbitol, corresponding to 27.5 mmole, was dissolved in 100 mL of deionized water in a separate beaker. Based on a hypothetical reaction stoichiometry of 3 parts hypochlorous acid to 1 part sorbitol, 124 mL of 5% NaOCl, corresponding to 82.4 mmole, was placed in a third beaker.

Appproximately 4 mL of the NaOCl solution was added to the first beaker containing the cobalt solution and the contents were stirred with a magnetic stir bar. This formed a black precipitate of hydrous cobalt oxide, most likely of the formula $CoO_2*xH_2O$. The sorbitol solution was then added to the stirred beaker containing the cobalt oxide precipitate, and the rest NaOCl solution was added as necessary, and until exhausted, to maintain the pH near 5.5. (the pH varied between 4 and 6.5 in practice).

The above steps were repeated in an additional three beakers except that the cobalt salt in the first solution was omitted. The NaOCl was added in this trial at the same rate as it was added in the first trial where the cobalt oxide precipitate was present.

Samples were taken from both of the reaction beakers 30 minutes after the NaOCl solution was exhausted, and were analyzed by ion chromatography. The data obtained is provided in Table 1:

TABLE 1

| Trial | Amount Present in Resulting Solution (g) | | |
|---|---|---|---|
| | Sorbitol | Sorbose | Ascorbic Acid |
| No Cobalt Oxide use | 4.8 | 0 | 0 |
| Cobalt Oxide used | 0.81 | 0.54 | 0.81 |

The results reported in Table 1 demonstrate that the hydrous cobalt oxide-hypochlorous acid system consumes sorbitol, and oxidizes it to sorbose and ascorbic acid. The results also demonstrate that without the cobalt oxide catalyst, no sorbose or ascorbic acid is produced, and little sorbitol is consumed by the hypochlorous acid. The presence of the ascorbic acid was confirmed with mass spectrometry.

EXAMPLE II

The procedure of Example I, for the trial with the cobalt salt, was repeated several times, except that the total amount of NaOCL solution used was varied from 0 mL to 124 mL. The data obtained is provided in Table 2:

TABLE 2

| Trial | Total Amount NaOCl Used (mL) | Ascorbic Acid Produced (g) |
|---|---|---|
| 1 | 0 | 0 |
| 2 | 21 | 0.690 |
| 3 | 41 | 1.27 |
| 4 | 83 | 1.87 |
| 5 | 103 | 1.42 |
| G | 124 | 0.81 |

The results reported in Table 2 demonstrate that the amount of ascorbic acid produced increased as the amount of NaOCl reagent was increased for trials 1–4. The decrease in yield, starting at trial 5 and continuing in trial 6, is most likely due to the rate of further oxidation of the ascorbic acid becoming faster than the rate of production of ascorbic acid. Thus it would appear that large excesses of hypochlorous acid should be avoided. The result of trial 1 also confirms that hypochlorous acid is a necessary reagent in the desired reaction.

EXAMPLE III

The procedure of Example I, for the trial with the cobalt salt, was repeated three additional times except that 5 g samples of glucose, sorbose, and KGA were separately substituted for the sorbitol and reacted with the indicated volume of NaOCl solution. The data obtained is provided in Table 3:

TABLE 3

| Starting Compound | Volume NaOCl Used (mL) | Ascorbic Acid Produced (g) |
|---|---|---|
| Glucose | 40 | 1.4 |
| Sorbose | 40 | 1.6 |
| KGA | 14 | 0.2 |

The results reported in Table 3 demonstrate that ascorbic acid can be synthesized from glucose in one step. This is very advantageous in that using D-glucose instead of D-sorbitol as the starting material in the synthesis of vitamin-C eliminates the hydrogenation step, and its associated costs, necessary to produce D-sorbitol from D-glucose.

The data presented in Table 3 also establishes that the hydrous cobalt oxide-hypochlorous acid system also works successfully to convert the by-products of the reaction (for example, using glucose as the lone starting material, the by-products would be sorbitol, sorbose, and KGA) to the desired product, ascorbic acid. This finding allows these by-products to be recovered during manufacture, and then reacted again with the hydrous cobalt oxide-hypochlorous acid oxidant to increase the yield of ascorbic acid and minimize waste and by-products. This finding is extremely important to the financial viability of invention.

EXAMPLE IV

The procedure of Example I, for the trial with the cobalt salt, was repeated, this time using only 30 mL of NaOCl solution. Approximately 200 mL of the product solution was centrifuged at 478 G for 15 minutes to separate the hydrous cobalt oxide precipitate from the liquid phase. The liquid product was decanted off and analyzed for ascorbic acid as in Example I. The recovered solid hydrous cobalt oxide was then added to a beaker containing 100 mL of deionized water. Then 100 mL of deionized water, with 5 g of sorbitol dissolved in it, was added to the cobalt oxide beaker. Reaction with an amount of NaOCl was performed, again making certain to maintain the pH of the reaction solution near 5.5. The product solution was again centrifuged to recover the solid hydrous cobalt oxide, and the liquid supernatant was also analyzed for ascorbic acid. In all, the original hydrous cobalt oxide precipitate was recovered and then reused in three subsequent reaction trials. The data obtained is provided in Table 4:

TABLE 4

| Trial | Volume NaOCl Used (mL) | Ascorbic Acid Produced (g) | R* |
|---|---|---|---|
| Initial Reaction | 30 | 1.0 | 3.5 |
| First Recycle | 10 | 1.1 | 1.1 |
| Second Recycle | 2 | 0.2 | 1.2 |
| Third Recycle | 0.7 | 0.1 | 1.0 | where R* = (moles NaOCl used)/(moles Ascorbic Acid produced)

The results reported in Table 4 establish that the hydrous cobalt oxide solids can be recycled and reused to synthesize additional ascorbic acid. It is apparent that if larger amounts of NaOCl were used, much higher yields of ascorbic acid would be achieved on the later recycle trials. The data in Table 4, particularly relating to the recycle trials, also establishes that the desired synthesis will proceed when considerably less than the hypothesized stoichiometric quantity (3:1) of hypochlorous acid to sorbitol is provided. Thus, for a balanced reaction, oxygen, most likely obtained from the surrounding air, must be an oxidant in the reaction. This gives the following balanced reaction equation:

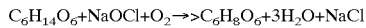

$$C_6H_{14}O_6 + NaOCl + O_2 \rightarrow C_6H_8O_6 + 3H_2O + NaCl$$

This finding makes it evident that less NaOCl can be used than was initially hypothesized (implying more oxygen is used) to produce same amount of ascorbic acid. This is a significant finding because of the relatively cheap cost of air as a reactant with respect to the cost of NaOCl.

Although the present invention has been described to specific exemplary embodiments thereof, it will be understood by those skilled in the art that variations and modifications can be effected in these exemplary embodiments without departing from the scope and spirit of the invention.

What is claimed is:

1. A process for producing ascorbic acid from a compound selected from the group consisting of glucose, sorbitol, sorbose, and 2-keto-gulonic acid, said process comprising:

oxidizing the compound with an effective amount of hypochlorous acid in the presence of a catalyst to produce ascorbic acid.

2. The process according to claim 1, wherein said hypochlorous acid is present in a stoichiometric amount.

3. The process according to claim 2, wherein said hypochlorous acid and said compound are present in a molar ratio between about 1:1 and about 3:1.

4. The process according to claim 3, wherein said hypochlorous acid and said compound are present in a molar ratio of about 1:1.

5. The process according to claim 1, wherein said catalyst is an oxide of cobalt.

6. The process according to claim 1, wherein said oxidation occurs at a temperature in a range from 1° C. to 100° C.

7. The process according to claim 1, wherein said oxidation occurs in an aqueous phase.

8. The process according to claim 7, wherein said aqueous phase is maintained at about a pH between 4 and 6.5.

9. The process according to claim 8, wherein said aqueous phase is maintained at a pH of about 5.5.

10. The process according to claim 1, wherein said compound is oxidized by an effective amount of oxygen and hypochlorous acid in the presence of said catalyst.

11. The process according to claim 1, comprising recycling by-products of the oxidation, unused amounts of compound or hypochlorous acid, and the catalyst such that the by-products, the unused amounts of compound or of hypochlorous acid and the catalyst can be used again in further oxidations.

12. A process for producing L-ascorbic acid in a single step from a compound selected from the group consisting of D-glucose, D-sorbitol, L-sorbose, and 2-keto-L-gulonic acid, said process comprising:

oxidizing the compound with an effective amount of hypochlorous acid in the presence of a catalyst to produce L-ascorbic acid.

* * * * *